United States Patent [19]

Aldrich

[11] Patent Number: Plant 5,320

[45] Date of Patent: Nov. 6, 1984

[54] ALMOND TREE

[75] Inventor: Clarence E. Aldrich, 10613 John Fox Rd., Hughson, Calif. 95326

[73] Assignees: Clarence E. Aldrich; Maryanne Aldrich, both of Hughson; Randal C. Aldrich, Waterford, all of Calif.

[21] Appl. No.: 470,518

[22] Filed: Feb. 28, 1983

[51] Int. Cl.[3] ..... A01H 5/03

[52] U.S. Cl. ..... Plt./30

[58] Field of Search ..... Plt./30

*Primary Examiner*—Robert E. Bagwill

*Attorney, Agent, or Firm*—Roger B. Webster

[57] ABSTRACT

An almond tree which is of medium size and vigor, open, and upright branching habit; sparsely foliated with small, lanceolate, acutely pointed leaves having a finely serrate margin and alternte, reniform glands; blooms heavily with white flowers; and is a regular and heavy producer of medium size, ovate, medium hard, thin shell nuts having small, ovate kernels.

1 Drawing Figure

BACKGROUND OF THE VARIETY

Field of the Invention

As an agriculturist, and attendant the operation and maintenance of my ranch located near Hughson, Stanislaus County, Calif., I frequent such ranch for the prupose of inspection, soil preparation for planting, cultivation, and irrigation, and—against the background of such activities—the present variety of almond tree was discovered.

CLASSIFICATION OF THE VARIETY

The present new and distinct variety of almond tree is embraced by Class 30, Plants, of the U.S. Patent Office Manual of Classification.

PRIOR VARIETIES

Among the existing varieties of almond trees which are known to me, and mentioned herein, are the Mission, Ne Plus, and Nonpareil (all unpatented); Merced U.S. Plant Pat. No. 1,730); and Carmel U.S. Plant Pat. No. 2,641). Reference is also made to the rootstocks Marianna and Nemaguard (both unpatented).

ORIGIN OF THE VARIETY

In the conduct of my activities on the aforesaid ranch, the present variety of almond tree was discovered by me growing, on a border bank, as a chance seedling; my attention having initially been attracted to such chance seedling by reason of its heavy bloom, and which coincided with that of the Nonpareil. After its discovery, I maintained such chance seedling under careful and continuing observation, and—upon recognition of certain novel and distinctive characteristics thereof—I determined to asexually reproduce it as a potential commercial variety.

ASEXUAL REPRODUCTION OF THE VARIETY

The present variety of almond tree was asexually reproduced—on my behalf and by a commercial nursery—by June budding on Nemaguard rootstock, and, in maturity, such reproduction ran true to the original tree (chance seedling) in all respects.

SUMMARY OF THE VARIETY

The present variety of almond tree is, characteristically, of medium size and vigor, open, and upright in branching habit; sparsely foliated with small, lanceolate, acutely pointed leaves having a finely serrate margin and alternate, reniform glands; blooms heavily with white flowers; and is a regular and heavy producer of medium size, ovate, medium hard, thin shell nuts having small, ovate kernels.

The present variety of almond tree is more particularly characterized by the heavy bloom being in coincidence with that of the Nonpareil and a very effective pollenizer for the latter, resulting in the Nonpareil setting extremely heavy crops of nuts.

The present variety of almond tree is further characterized, in comparison to Ne Plus, Nonpareil, Merced, and Carmel, by nuts having an extremely thin hull at green stage, and which hull is forty to fifty percent thinner than said prior varieties. Such thin, green-stage hull is of substantial advantage as it permits the tree of the present varity to bear and withstand heavy nut yields without the usual stress on limbs as occurs with thicker hulled varieties.

The present variety of almond tree is still further characterized:

By nuts which have a paper thin hull at harvest, permitting faster after-rain drying, and ease of hulling;

By nuts having well-sealed shells—minimizing worm infestation and damage; and

By nuts which hold well on the tree and yet knock with the ease of the Carmel and Ne Plus and regardless of weather conditions.

The present variety of almond tree—which is compatible with the Marianna rootstock—has generally similar growth characteristics of the Mission, being very upright, and sparse of foliage with small leaves, but—in comparison—blooms and harvests much earlier, the nuts having a thinner hull, knock much easier, and the shell is not as hard.

BRIEF DESCRIPTION OF THE DRAWING

The drawing is an illustration, by photographic reproduction in color, of a twig with leaves, and attached nuts; separate out-of-hull nuts, one nut having the shell partially broken away to expose the kernel; and separate out-of-shell kernels.

DESCRIPTION OF THE VARIETY

The botanical details of this new and distinct variety of almond tree—with color definitions in common color terms—are as follows:

TREE

Density: Open.
Size: Medium.
Vigor: Medium.

TRUNK

Size: Stocky.
Texture: Medium.

BRANCHES

Size: Slender.
Texture: Medium.
Lenticels: Numerous; medium size.
Branching habit: Upright.
Color:
*New wood.*—Red. Dull.
*Mature wood.*—Red to brown. Dull.

FOLIAGE

Quantity: Sparse.

LEAVES

Size: Small.
*Average length.*—2".
*Average width.*—$\frac{5}{8}$".
Shape: Lanceolate; acutely pointed.
Thickness: Thin.
Texture: Smooth.
Margin: Finely serrate.
Petiole: Long: Slender.
Glands: Average number — 4. Alternate. Small. Reniform. Red.- green.
Stipules: Wanting.
Color:
*Top side.*—Medium dark green.
*Under side.*—Medium light green.

BLOOM

Amount of bloom: Heavy.
Color: White.
Blooming period:
*Date of first bloom.*—Feb. 18, 1982 (pink Bud — Feb. 27, 1982).
*Date of full bloom.*—Mar. 4, 1982. Coincides with Nonpareil, but slightly longer bloom period.

CROP

Bearing: Regular bearer.
Productivity: Heavy.
Distribution of nuts on tree: Well distributed.
Harvest period: Medium. Coincides with Merced, follows Ne Plus, before Carmel snd Mission.
Tenacity: Hands well on tree. Very easy to harvest. Very easy to hull.

HULL

Outer surface: Smooth.
Pits: Wanting.
Form: Regular.
Thickness: Thin.
Flesh: Medium tough.
Suture: Flat depressed.
Color: Light green with a silvery sheen. Blushed with yellow color.
Dehiscence: Opens freely.
Splitting: Along suture.

NUT

Size: Medium.
*Average length.*—29 mm.
*Average width.*—19 mm.
*Average thickness.*—15 mm.
*Average weight.*—240 Nuts per pound.
Form:
*Length/width.*—Ovate.
*Width/thickness.*—Medium.
Shell: Medium hard. Thin. Smooth.
Outer shell: Firm to crumbling.
Inner shell: Hard. Well sealed.
Color: Medium light brown.
Pits: Small. Numerous. Deep. Irregular.
Base: Dorsally oblique.
Stem scar: Small. Obtuse.
Apex: Acute.
Wing: Narrow. Thin. Tapered toward apex.
Inner surface: Medium colored.
Ventral streak: Dark. Broad. Long. Point acute.
Percentage of kernel to nut: 59.4%.

KERNEL

Size: Small.
*Average length.*—22 mm.
*Average width.*—12 mm.
*Average thickness.*—9 mm.
*Average weight.*—28 Per ounce.
Form:
*Length/width.*—Ovate.
*Width/thickness.*—Medium.
Base: Ventrally oblique.
Stem Scar: Small.
Apex: Acute.
Texture: Wrinkled.
Pellicle: Thin.
Pubescence: Medium.
Color: Dark brown.
Number of doubles: Few.
Flavor: Normal.
Quality: Good.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, particularly characterized by heavy bloom before Mission but coincident with Nonpareil; and by the regular and heavy production of medium hard shell, well sealed nuts which hold well, knock easily, and have an extremely thin hull at green stage and a paper thin hull at harvest; the harvest being before Carmel and Mission, with Merced, and after Ne Plus.

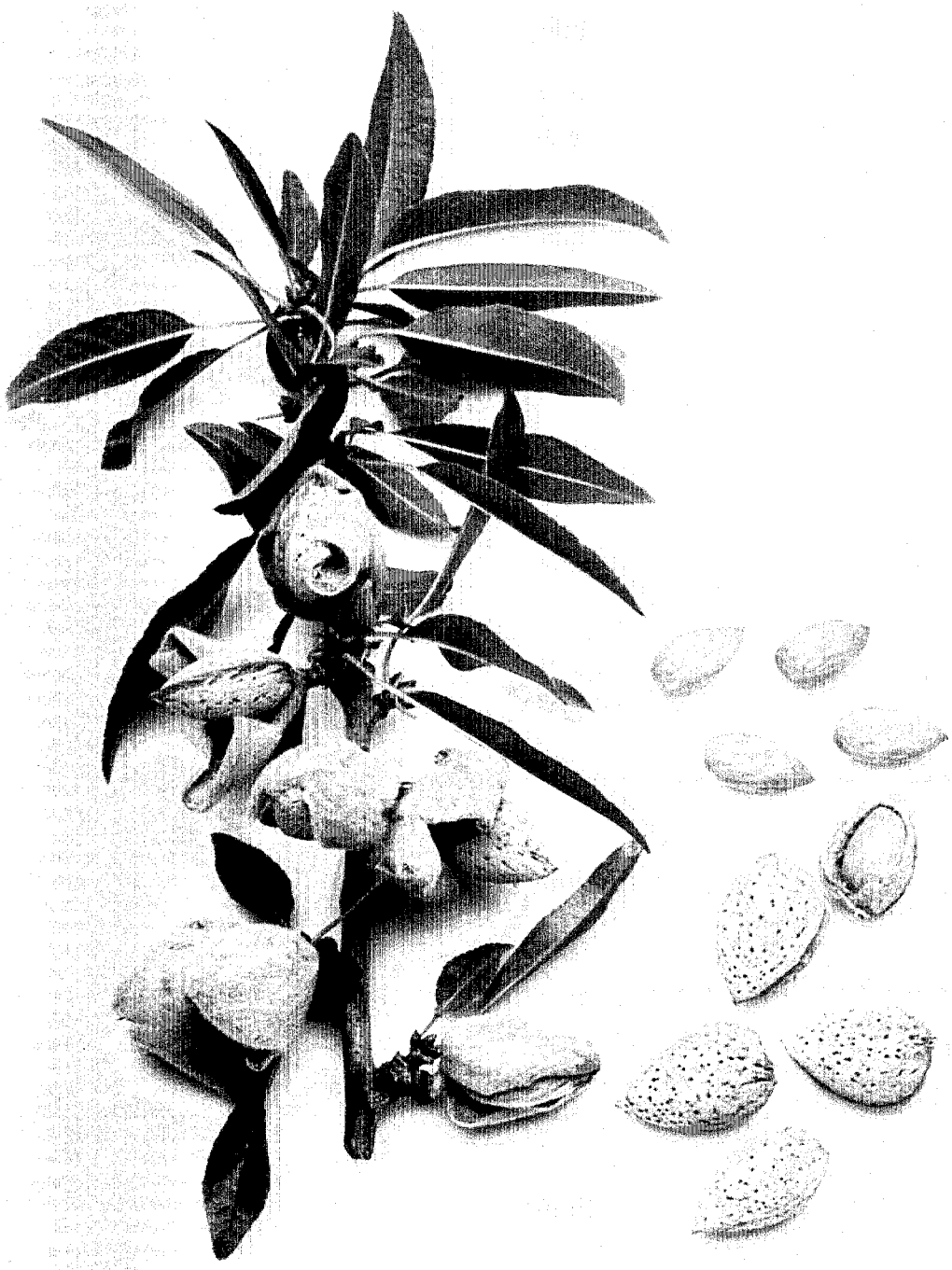

* * * * *